United States Patent [19]
Avitall

[11] Patent Number: 5,730,704
[45] Date of Patent: *Mar. 24, 1998

[54] LOOP ELECTRODE ARRAY MAPPING AND ABLATION CATHETER FOR CARDIAC CHAMBERS

[76] Inventor: Boaz Avitall, 4868 N. Ardmore Ave., Milwaukee, Wis. 53217

[*] Notice: The term of this patent shall not extend beyond the expiration date of Pat. No. 5,555,883.

[21] Appl. No.: 646,684

[22] Filed: May 6, 1996

Related U.S. Application Data

[63] Continuation of Ser. No. 380,204, Jan. 30, 1995, Pat. No. 5,555,883, which is a continuation of Ser. No. 156,283, Nov. 22, 1993, abandoned, which is a continuation-in-part of Ser. No. 909,869, Jul. 7, 1992, Pat. No. 5,263,493, which is a continuation-in-part of Ser. No. 840,162, Feb. 24, 1992, abandoned.

[51] Int. Cl.$^6$ ........................................................ A61B 5/04
[52] U.S. Cl. .................................... 600/374; 606/45
[58] Field of Search ............................ 128/642; 606/39–50; 607/115, 116, 119, 122, 125, 126

[56] References Cited

U.S. PATENT DOCUMENTS

| | | |
|---|---|---|
| 3,805,791 | 4/1974 | Seuberth et al. |
| 4,033,331 | 7/1977 | Guss et al. |
| 4,522,212 | 6/1985 | Gelinas |
| 4,581,017 | 4/1986 | Sahota |
| 4,638,802 | 1/1987 | Okada |
| 4,641,649 | 2/1987 | Walinsky et al. |
| 4,660,571 | 4/1987 | Hess et al. |
| 4,664,120 | 5/1987 | Hess |
| 4,677,990 | 7/1987 | Neubauer |
| 4,682,596 | 7/1987 | Bales et al. |
| 4,699,147 | 10/1987 | Chilson et al. ............... 128/642 |
| 4,777,955 | 10/1988 | Brayton et al. |
| 4,785,815 | 11/1988 | Cohen |
| 4,785,823 | 11/1988 | Eggers et al. |
| 4,869,248 | 9/1989 | Narula |
| 4,882,777 | 11/1989 | Narula |
| 4,920,980 | 5/1990 | Jackowski |
| 4,922,912 | 5/1990 | Watanabe |
| 4,940,064 | 7/1990 | Desai |
| 4,960,134 | 10/1990 | Webster, Jr. |
| 5,010,894 | 4/1991 | Edhag |
| 5,056,526 | 10/1991 | Khalil |
| 5,078,717 | 1/1992 | Parins et al. |
| 5,117,828 | 6/1992 | Metzger et al. |
| 5,156,151 | 10/1992 | Imran |
| 5,207,686 | 5/1993 | Dolgin |
| 5,263,493 | 11/1993 | Avitall ........................... 128/642 |
| 5,365,926 | 11/1994 | Desai ............................ 128/642 |
| 5,555,883 | 9/1996 | Avitall ........................... 128/642 |

*Primary Examiner*—Jennifer Bahr
*Assistant Examiner*—Samuel Gilbert
*Attorney, Agent, or Firm*—Haugen and Nikolai, P.A.

[57] ABSTRACT

A cardiac arrhythmia mapping and ablation catheter has a main catheter that is provided with a loop-shaped mapping and ablation system attached to its distal end in which the loop is optionally adjustable or of relatively fixed shape resumable upon deployment. The loop carries an electrode array including a plurality of separately operable recording (mapping)/ablation electrodes in conductive relation to the external environment and arranged in spaced serial relation along the loop. Insulated conductors connect the electrodes electrically with input/output devices outside the catheter for mapping the electrical activity of the chamber wall contacted and ablating tissue as indicated. A distal extension or guide member may optionally be provided to adapt the loop specifically to addressing the tricuspid annulus or other desired location.

16 Claims, 7 Drawing Sheets

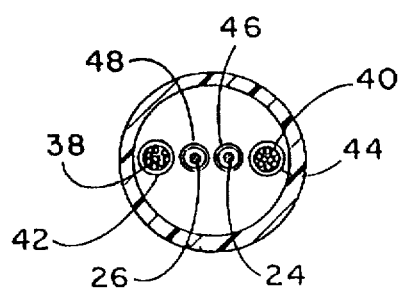
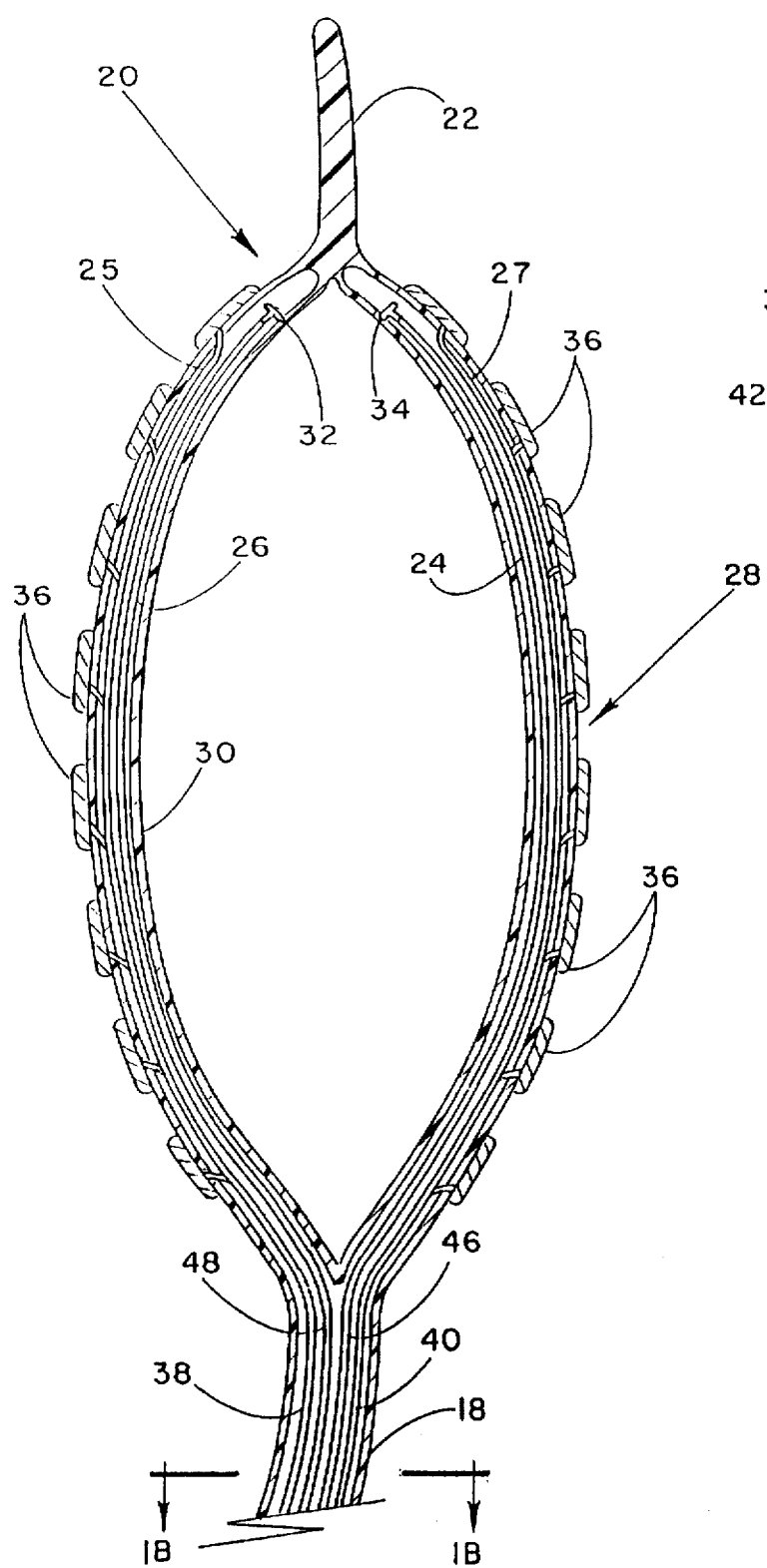

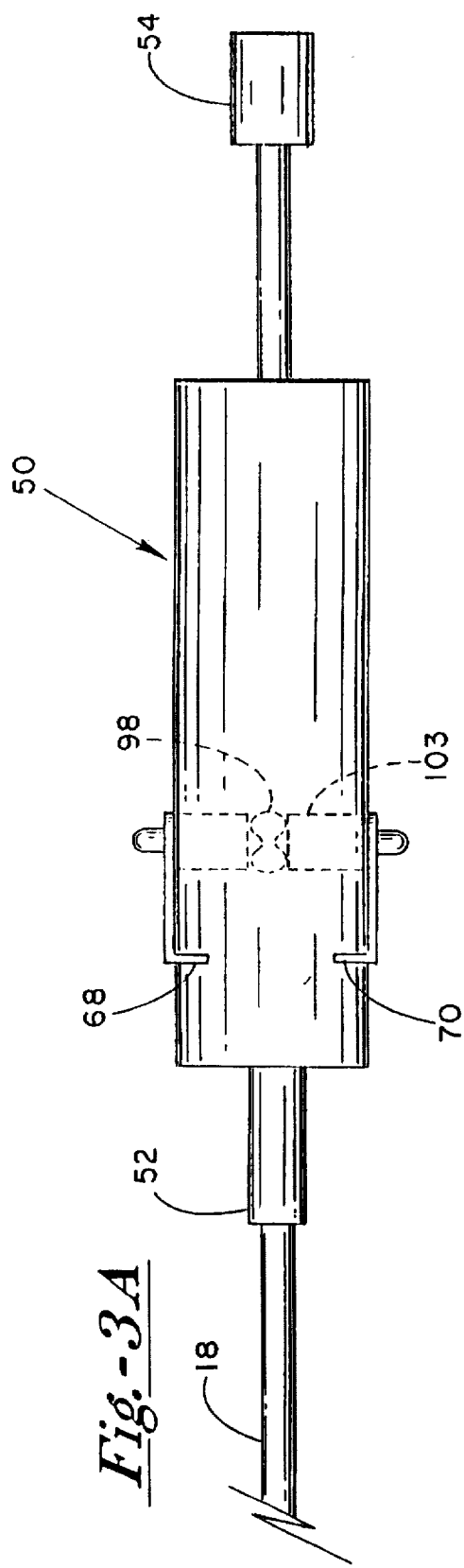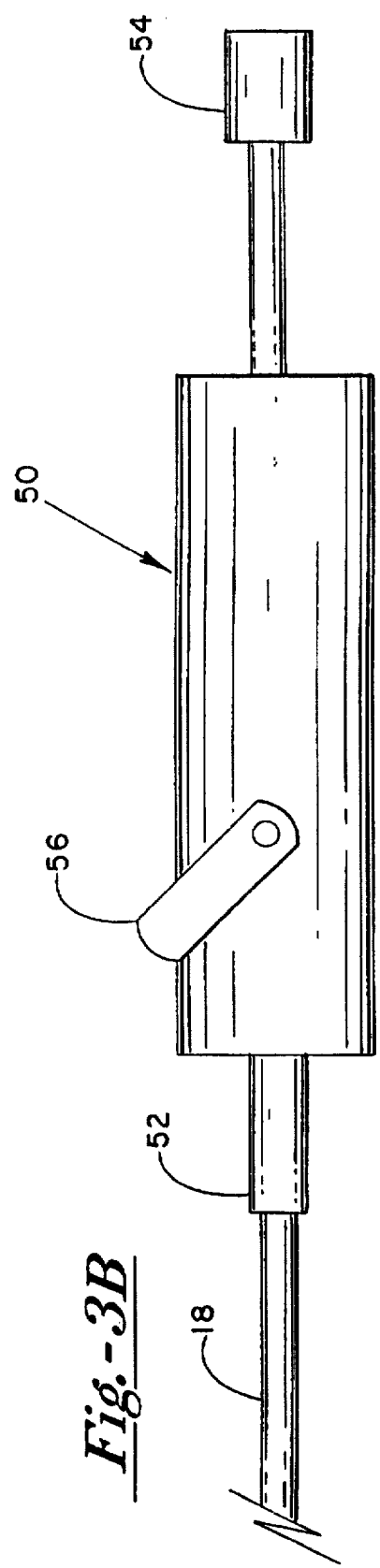

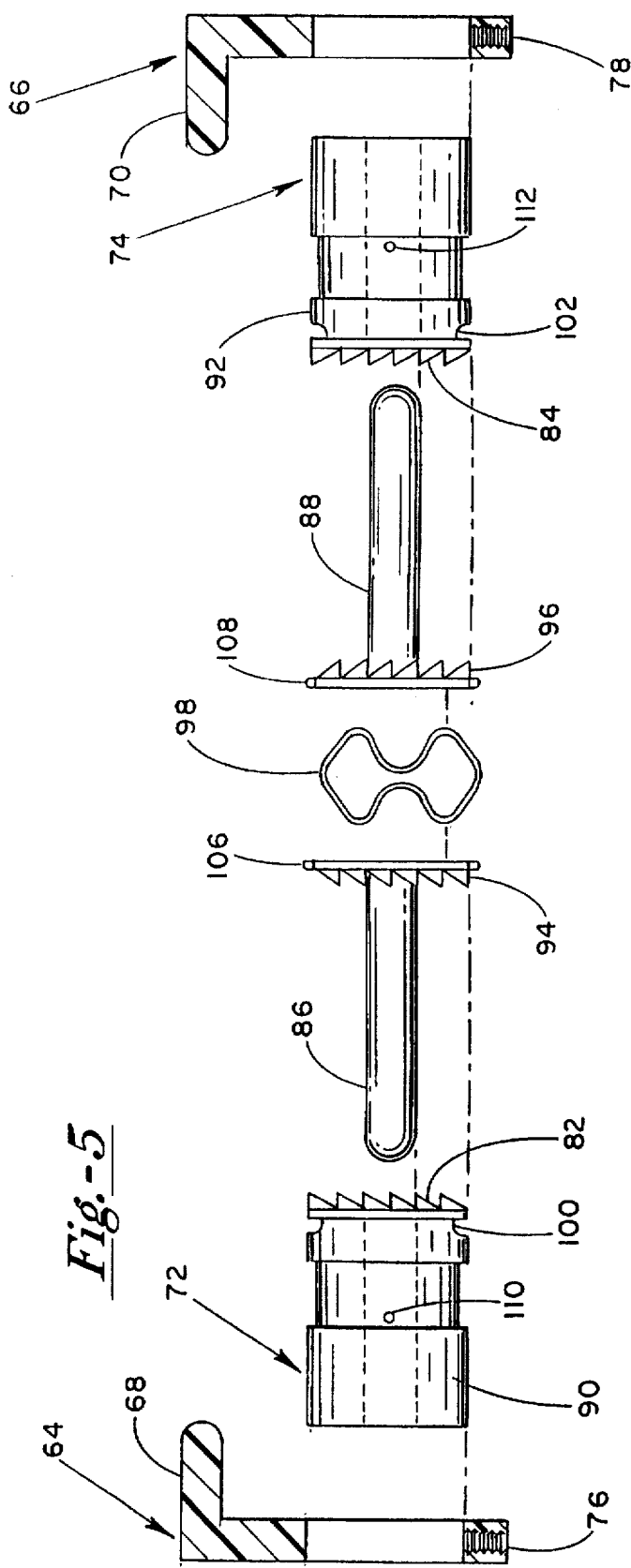

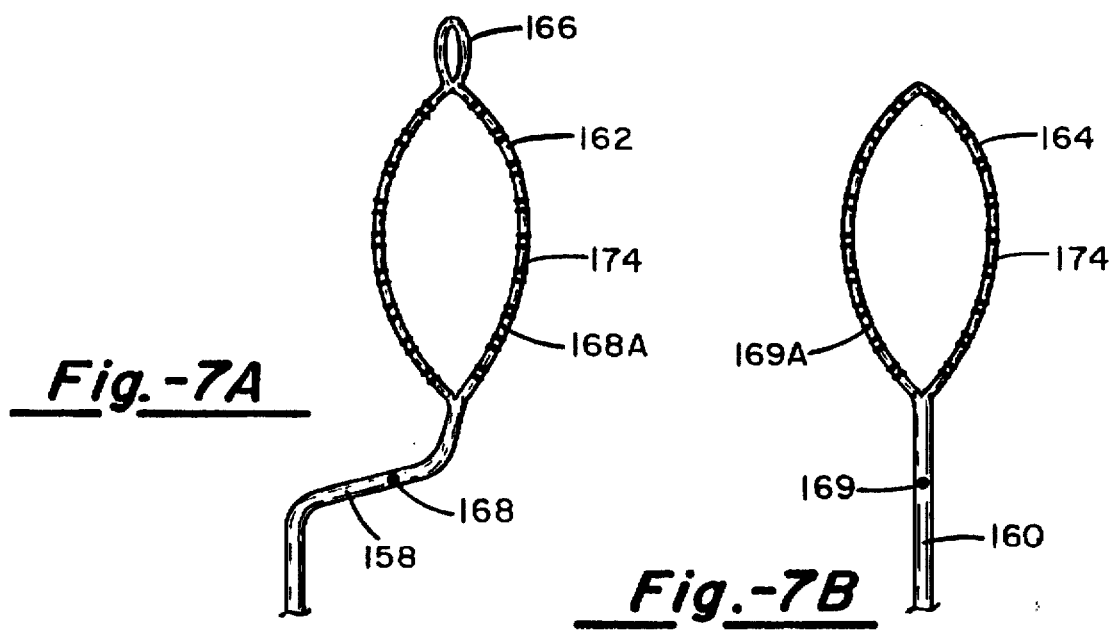
*Fig.-7A*
*Fig.-7B*
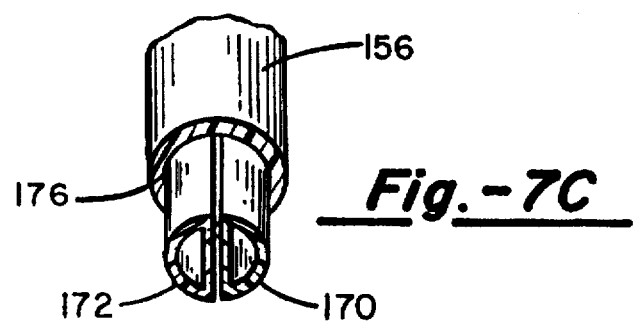
*Fig.-7C*

LOOP ELECTRODE ARRAY MAPPING AND ABLATION CATHETER FOR CARDIAC CHAMBERS

BACKGROUND OF THE INVENTION

I. Cross-Reference to Related Application

This is a Continuation of application Ser. No. 08/380,204, filed on Jan. 30, 1995, now U.S. Pat. No. 5,555,885 which is a continuation of Ser. No. 08/156,283, filed Nov. 22, 1993 now abandoned, which is a continuation-in-part of Ser. No. 07/909,869, filed Jul. 7, 1992 and now U.S. Pat. No. 5,263,493, which is a continuation-in-part of Ser. No. 07/840,162, filed Feb. 24, 1992, now abandoned.

Reference is further made to applications Ser. Nos. 07/835,553 and 07/840,026 of common inventorship. Both of these cross-referenced applications also are directed to improved catheters.

II. Field of the Invention

The present invention is directed generally to an improved catheter usable in the field of cardiac arrhythmia recording (mapping) and ablation. More particularly, the invention is directed to the use of a deflectable, optionally size and shape adjustable, electrode array carrying loop shaped catheter device which allows the operator to rapidly map certain heart chamber areas and including the tricuspid annulus to electrically map to tissue and optionally ablate tissue sections where pathways that cause cardiac arrhythmias are identified using one or more electrodes in the array that can be most closely positioned to the site that should be ablated.

III. Discussion of the Related Art

Normal cardiac pacing, in a healthy heart, is controlled by a special structure known as the sinoatrial node (SA node). This is the natural pacemaker of the heart and is a specialized tissue located within the muscle walls of the right atrium. The SA node provides impulses which dominate the inherent or natural rhythmic contractions of the heart atria and the ventricles. This dominance or control involves the transmission of ionic impulses through cardiac conduction pathways in the atria and the ventricles which cause the heart to contract and relax in an orderly sequence at a rate dictated by the SA node. This sequence ensures that blood flow to the systemic circulation or the pulmonary system will be maximized with each ventricular contraction. The SA node has its own inherent rate which can be modified by signals from the nervous system. In response to excitement, physical activity, etc., the sympathetic and parasympathetic nervous systems react to modify the rate.

A depolarization impulse begins with the SA node and spreads as an electrical wave from its location in the right atrium across to the left atrium and down toward the transition zone between the atrium and the ventricles where another node, known as the atrioventricular (A-V) node or junction, is located. This impulse conducts through the AV node in a slower fashion and continues to a common pathway known as the bundle of His between the right and left ventricles, then into multiple paths called right and left bundle branches, each bundle branch supplying one ventricle. These bundle branches then divide into an extensive network of finer paths of conducting tissue which spread from the inner to the outer surfaces of the heart and which are referred to as the Purkinje fibers. These fibers feed the depolarization impulse into all portions of the ventricular myocardium.

As long as this system is intact, impulses are transmitted normally and cardiac rhythm is maintained. The natural impulse or current flow in the cardiac conduction system, however, may be interrupted or altered by congenital defect, disease or external trauma which can cause the formation of scar tissue. When a sufficiently severe injury or a congenital defect is present in the cardiac conductive pathways or in the ventricular myocardium, the electrical impulses are not transmitted normally and rhythmic disturbances known as cardiac arrhythmias can occur. With respect to such disturbances, the term bradycardia is used to describe an abnormal slowing of the cardiac contractions and the term tachycardia is used to describe abnormally rapid heart action. While either of these conditions can endanger the life of the patient, tachycardia is more serious, particularly in patients having underlying heart disease.

Ventricular tachycardia and other ventricular arrhythmias have been treated with a number of drugs such as lidocaine, quinidine and procainamide. In cases of excessive sympathetic nervous activity or adrenal secretion, Beta blocking drugs have been used. In cases where drug therapy has been ineffective in preventing tachyarrhythmias, certain surgical procedures have been used to ablate the arrhythmogenic tissue either from the atrium or the ventricles. This approach involves extensive surgery in which an incision is made through the pericardium and heart muscle to enable location of the arrhythmogenic tissue sites, which are then ablated by being frozen or surgically removed to be replaced by scar tissue.

Open-heart surgery, however, is a high risk radical approach which requires a prolonged period of hospitalization and recuperation; a less traumatic solution is needed. In response, catheters of various types have been devised and used for diagnosing and treating a number of cardiac abnormalities to avoid the trauma of open-heart surgery. For example, as a method for resolving atherosclerotic plaque build up, stenotic lesions are now routinely opened by the use of balloon angioplasty. In this procedure, a balloon carrying catheter is navigated through the patient's vascular system to the location of the stenosis. The balloon is inflated by fluid injected through a lumen of the catheter to apply pressure to compress the stenosis against the wall of the clogged vessel, thereby opening it.

Catheter devices have also been used to locate and ablate cardiac conduction pathways. One such device is shown in U.S. Pat. 4,785,815, in which a catheter tube carries at its distal end at least one electrode for sensing membrane potentials within the heart, together with a heating device for ablating at least a portion of the pathway located by the sensing device. Another thermal ablation catheter for microtransection or macrotransection of conduction pathways within the heart, which uses a resistive heating element at its distal end for highly localized treatment, is illustrated and described in U.S. Pat. No. 4,869,248. These devices are generally effective once the ablating element is properly positioned at the localized area of interest. A catheter device of the class described has also been developed which employs a single handle operated deflection wire. Such a device is disclosed in U.S. Pat. No. 4,960,134.

Most present cardiac tissue ablation procedures involve the use of radio frequency (RF) electrical current transmitted to the tissue via a catheter which is positioned as closely as possible to the arrhythmogenic site within the atria or ventricles. Radio frequency electrical current heats the tissue surrounding the catheter, creating a discrete, dense lesion. In order for the patient to be cured of the arrhythmia, the lesion must be created in the area from which the arrhythmia originates. Improvement in the maneuverability of such devices and in the ability to access areas difficult to reach with present devices but which are common sources of abnormal rhythm would greatly assist optimization of arrhythmia location (mapping) and precise positioning of the catheter electrodes for ablation.

In many patients with cardiac arrhythmias, the tissue that causes the abnormal rhythm is located in the right side upper chamber (atrium) at or near the tricuspid ring. The most appropriate location for ablation is defined by mapping a large area of tissue in order to identify the earliest electrical activity. The mapping process and the identification of the anatomical location of the catheter is at times a challenging and laborious procedure which as a result subjects the operator and patient to prolonged x-ray radiation.

Unlike with procedures for ablation of tissues around the mitral valve annulus, where a coronary sinus catheter readily provides crucial information as to the location of the arrhythmogenic tissue and also serves as a guide to the placement of the ablation catheter, no such structure is present at the right side of the heart around the tricuspid valve. A device which provided both the ability to rapidly map the entire tricuspid ring and areas adjacent to it, as well as the ability to apply the ablation energy to the most desirable location using the same catheter would not only expedite the ablation procedure, but also make it easier and more effective.

SUMMARY OF THE INVENTION

The present invention provides an unique mapping and ablation catheter device that provides both the ability to rapidly map cardiac chambers and also has a special adaptation to address the entire tricuspid ring and areas adjacent to it, as well as the ability to apply the ablation energy to the most desirable location using the same electrode. This capability makes it easier to map the area of interest, and expedites and makes the ablation procedure more effective. The present invention is a new catheter design which incorporates a distal loop segment that may be of a predetermined, relatively fixed open loop shape which the loop resumes when deforming force is removed, e.g., when it emerges from a main catheter lumen or sheath, or, optionally, one that can be opened and closed by tensing drawstring wires extending from the catheter handle. In one application, the loop is of a size designed to fit around the tricuspid valve.

The most distal part of the loop may be provided with an extension anchor or distal guide segment which may be an addition loop formed as an extension of the main loop, typically in the form of a short length of flexible polyurethane tubing. The guide segment can be inserted into the most anterior angle of the tricuspid ring and used to help anchor and guide the positioning of the main loop. Without the extension, the device is suitable for addressing many other cardiac areas. While dimensions are not critical, the extension is normally about 4 French in diameter and less than an inch (nominally 18 mm) long. As indicated, the loop extension or guide provides an anchor for the loop at its distal end and the catheter shaft, from which the loop extends, is designed to be advanced into the inferior vena cava or introduced at another convenient place and provide the anchor for the loop at its proximal end.

The loop is equipped with serially distributed electrodes spaced apart optionally in pairs and connected in a manner to allow recording from any and all individual electrode locations in the loop as to map around the tricuspid ring. In one arrangement, each electrode back side is shaved or flattened to permit the majority of the exposed surface to be in contact with the tissue and not simply with the blood. In one embodiment, the electrodes had a length of about 4 mm and were spaced about 2 mm apart. Pairs of ring electrodes about 2 mm long spaced about 1 mm apart with the sets of pairs spaced about 8 mm apart may be preferred to accomplish more localized mapping and by connecting both electrodes simultaneously, one can accomplish an effective ablation.

One embodiment includes two deflection wires that are threaded in opposed relation along opposite sides of the loop arc extending thorough the loop and the main catheter lumen to a handle operable to control the size and shape of the loop. In this configuration, when these control wires are in their normal (untensioned) state, the loop remains closed with the opposite sides of the loop arc substantially parallel. Similar amounts of tension applied to both wires causes the loop to open symmetrically and remain in a constant position corresponding to the tensions applied; however, the pulling or tensing of but a single wire causes the loop to open asymmetrically and deflect toward the side of the loop arc opposite that being deflected. The loop is further mounted on a rigid sheath of strong thermoplastic material which is capable of sustaining the high pull forces on the deflection wires without damage, as well as maintaining a predetermined shape modified by heating the shaft and bending as required for the particular procedure. Once the thermoplastic catheter shaft is cooled, the angulation which was applied to the catheter during heating will be maintained. This construction enables the operator to rotate the catheter loop and control the location of the tip in a more positive manner.

The predetermined selected shape of the shaft allows the operator to advance the catheter loop sheath carrying the loop more readily into the tricuspid ring from the inferior vena cava. The configuration is such that rotation of the shaft causes the loop to rotate along the axis of the tricuspid ring, which allows the operator to map atrial and ventricular electrical activity at the posterior and anterior aspect of the tricuspid ring. The operator can readily change the catheter deflection by applying tension on one of the pull wires to change the loop angle with respect to the catheter shaft, thus providing greater flexibility of angles and shapes to accommodate the varying anatomical positions of the tricuspid ring.

In another embodiment, the shape of the deployed loop itself is predetermined or relatively fixed. The distal segment including the loop is deployed from a lumen access or sheath of the main catheter in the chosen chamber where it resumes the predetermined shape. The extended distal segment including the loop may deploy directly from the catheter lumen or sheath, but preferably includes a short proximal flexible tubing segment leading to the loop. A device such as a pull wire may be provided in the proximal tubing segment or fixed at some point on the loop itself to provide a system to adjust the posture or deflection of the loop relative to the main catheter or sheath. The fixed shape loop, while somewhat less versatile than the adjustable shape, makes it easier to fit or position the loop to produce better electrode contact with certain specific internal surface areas. In this manner, a variety of specialized shapes of open loops may be provided particularly to address heart valve areas. The specialized shaped loops may optionally be provided with extensions, i.e., anchor or guide appendages, where beneficial.

BRIEF DESCRIPTION OF THE DRAWINGS

In the drawings, wherein like numerals are utilized to designate like parts throughout the same:

FIG. 1A is a greatly enlarged schematic view of the electrode array loop of the invention;

FIG. 1B is a crossection view along lines 1B—1B of FIG. 1A;

FIGS. 3A and 3B are schematic side and top views, broken, and partially in section, with parts cut away of a catheter and handle for use with the electrode array;

FIG. 5 is a greatly enlarged exploded plan view of parts of the handle of FIGS. 3A, 3B and 4;

FIGS. 7A-7B are further schematic views of other possible fixed loop configurations; and FIG. 7C is a fragmentary view of shapes of the loop section as they fit together within the sheath or catheter lumen.

DETAILED DESCRIPTION

Figure 2A:
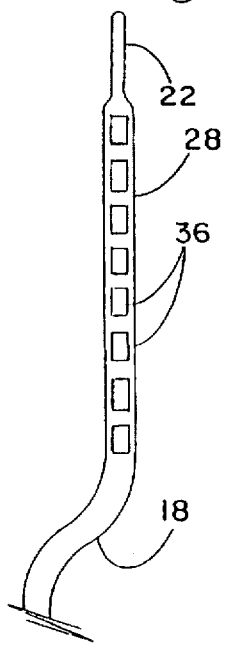
FIGS. 2A-2E are schematic views of the electrode array loop in a variety of dispositions and degrees of openness.
Figure 2B:
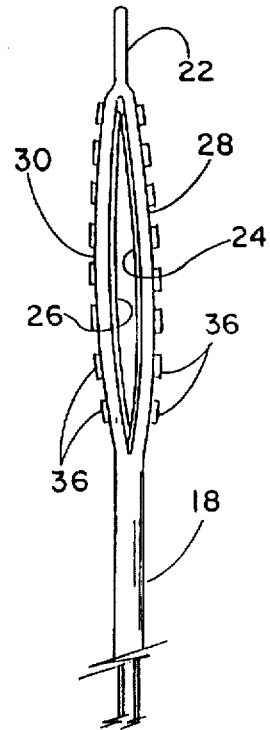
Figure 2C:
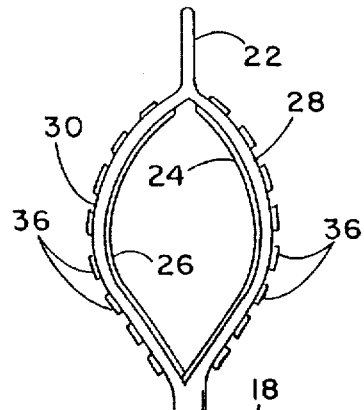

Certain embodiments of the invention will next be described with reference to the several views of the drawings. The loop shown generally at 20 in the enlarged schematic view of FIG. 1A is made of thick but flexible reinforced polymer tubing (typically 1.7 mm in diameter) which is configured to form an ellipse when opened. The loop of polymer tubing, in this embodiment, is provided with a distal extension or appendage 22 also of a compatible polymeric material such as polyurethane optionally in the form of a smaller loop. By way of example, the extension 22 may be 18 mm long by 4 French in diameter. The loop 20 also includes a pair of deflection control wires 24 and 26 each anchored to the distal portion of the respective half of the tubular elliptical loops 28 and 30 by respective T-shaped pins 32 and 34. The loop further contains a series of spaced tubular noble metal electrodes shown in part at 36 on either half of the elliptical loop which are further attached to individual respective insulated conductor wires as at 25 and 27 which may be bundled as represented by 38 and 40. Both the deflection control wires 24 and 26 and the conductors 38 and 40 are threaded through the respective loop lumen and the main catheter sheath to the control handle. The deflection control wires 24 and 26 thread through individual carrier tubes 46 and 48, respectively.

As better seen in FIG. 2A, when the loop is fully closed, it forms a substantially straight line. While dimensions are not critical, the length of the long axis is typically about 6 cm and the loop extension segment 22 about 18 mm. The electrodes 36 are preferably made of platinum tubing 2 mm thick and 4 mm long.

Prior to securing the electrodes, each of the platinum tubing segments 36 is attached to a respective low resistance conductor wire as at 25 and 27 nominally 0.08 mm in diameter that are threaded through small holes in the tubing (not shown). Each set of conductor wires 38, 40 is inserted into a polymer, preferably polytetrafluoroethylene (PTFE), tube as at 42, 44 that is disposed inside and extends the length of the main catheter shaft 18. This protects the conductor wires and carries them to an electrical connector which is mounted on a short cable on the proximal end of the catheter handle (FIGS. 3A and 3B).

Figure 6A:
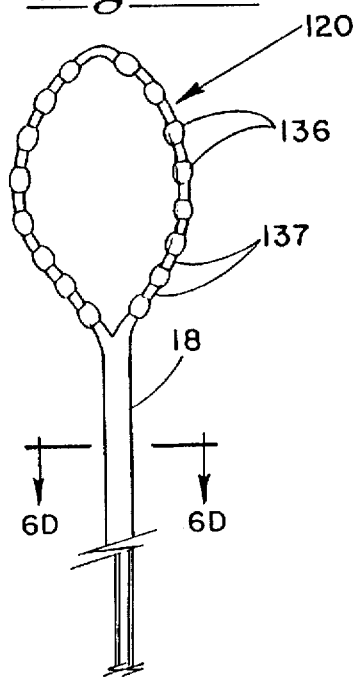
FIGS. 6A-6D are schematic views of the electrode array loop showing a variety of deflection dispositions or possibly fixed loop shapes.
Figure 6B:
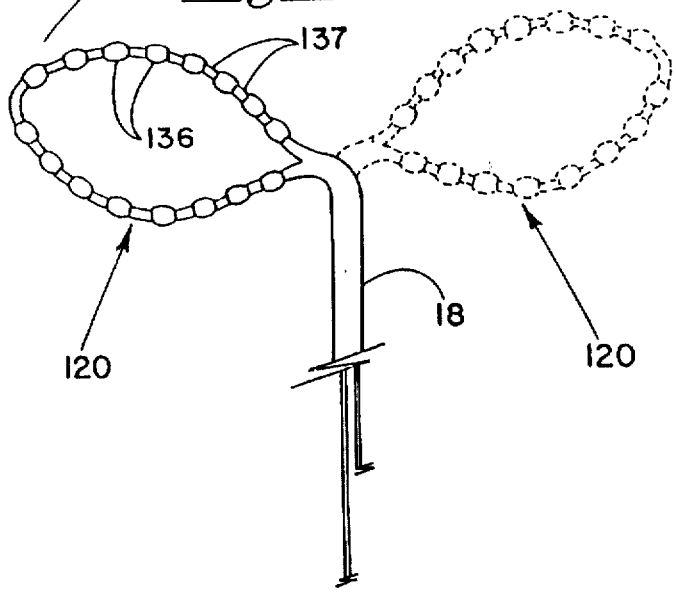
Figure 6C:
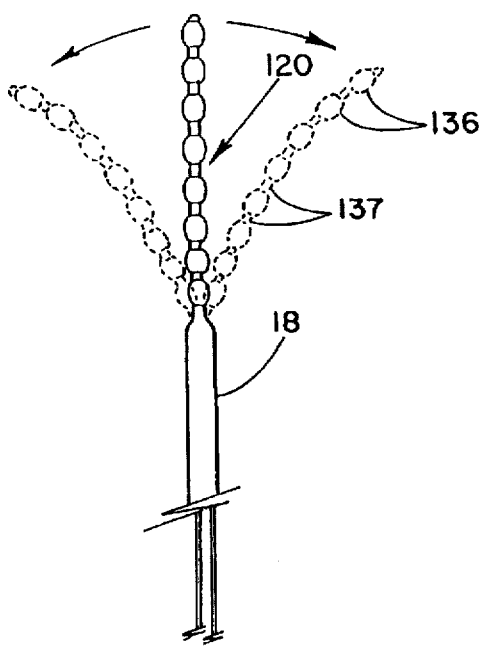

The tubular electrodes are also illustrated in FIGS. 6A-6C where a full view of the tubular segments is shown at 136. The electrodes 136 are likewise attached to individual respective insulated conductor wires shown bundled at 138 and 140 carried in tubes 142 and 144, respectively, in FIG. 6D. As with the electrodes 36, the electrodes 136 are typically 4-5 mm or less in length with any sharp edges removed and are separated by gaps 137 which may be any desired length but are typically about 2 mm. The control wire carrier tubes 146 and 148, respectively, carry control wires 124 and 126 as illustrated in the embodiment of FIGS. 1A and 1B. Control of individual electrodes for mapping activity and for ablation is the same as that of FIGS. 1A-1B and 2A-2E.

Regardless of electrode configuration, the main catheter shaft 18, then, contains four PTFE tubes, as shown in FIG. 1B, tube 42 carries the bundle of electrical conductor wires from the side 30 of the electrodes on the loop 20, 44 carries the bundle of electrical conductor wires from the side 28 of the electrodes on the loop 20. Tube 46 carries the pull wire 24 for the deflection of the lower loop segment 28 and 48 carries the pull wire 26 for the deflection of the loop segment 30. The deflection wires 24, 26 are preferably stainless steel, nominally 0.22 mm thick and attached to the T-shaped pins 32 and 34 (FIG. 1A) by crimping the respective pin onto the wire. The T-shaped pin and the pull wire are inserted into the loop tubing through a small hole in the inner aspect of the loop tubing. Each T-shaped pin may be imbedded into the tubing and secured with a compatible adhesive such as polyurethane glue.

Figure 2D:
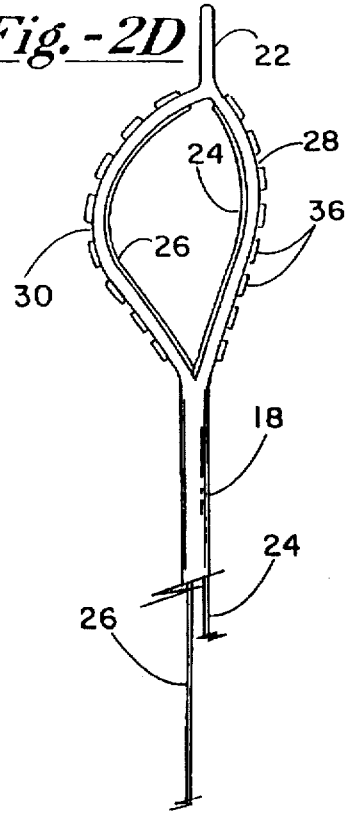
Figure 2E:
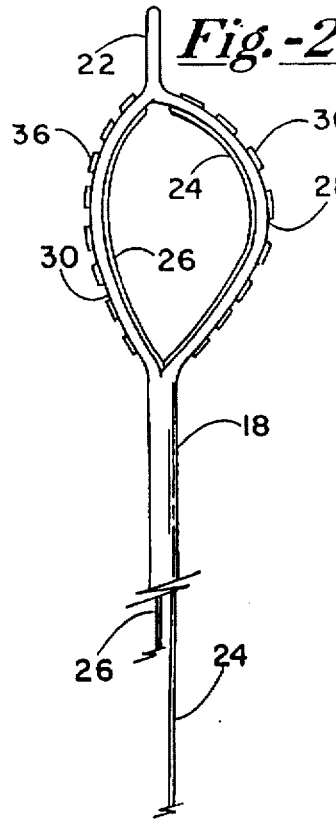

As shown in FIGS. 2A-2E, when tension is applied to the deflection wires 24, 26, the upper and lower segments 28 and 30 will bend to form the loop which will result in the loop opening (2C). When the wire 26 is pulled alone or to a greater degree, the loop will open and deflect downward as shown in FIG. 2D. The reverse occurs when the lower wire 24 is pulled as illustrated in FIG. 2E.

Figure 6D:
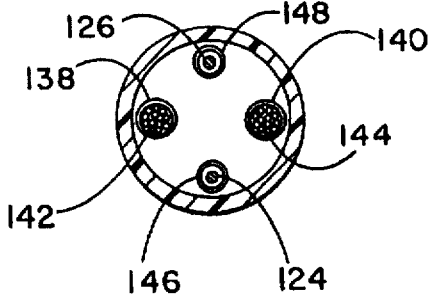

In FIG. 6D, control wires 124 and 126 are shown offset with respect to the conductor bundles 138 and 140 as opposed to the essentially in-line configuration of FIG. 1B, which is parallel to the plane of the undeflected electrode loop in its normal position parallel to the main catheter segment 18. The essentially 90° offset arrangement shown represents an exaggerated illustration pertaining to the use of the control wires for side-to-side deflection of the loop as shown in FIGS. 6B and 6C. Even with the in-line arrangement of FIGS. 1A and 1B, some side-to-side loop deflection control can be accomplished in addition to the loop shape control; and, it will be appreciated that any desired degree of offset, symmetrical or asymmetrical, can be employed.

Although dimensions are not critical, the distal portion of the main shaft 18 of the catheter is preferably about 8 F in diameter and made of a reinforced thermosetting polymer tubing that can be reshaped by heating. The tubing is designed to be heated and shaped prior to use. Once cooled, the new shape is maintained with minimal deflection of the shaft even when high tension is applied to the loop deflection control or pull wires.

Figure 4:
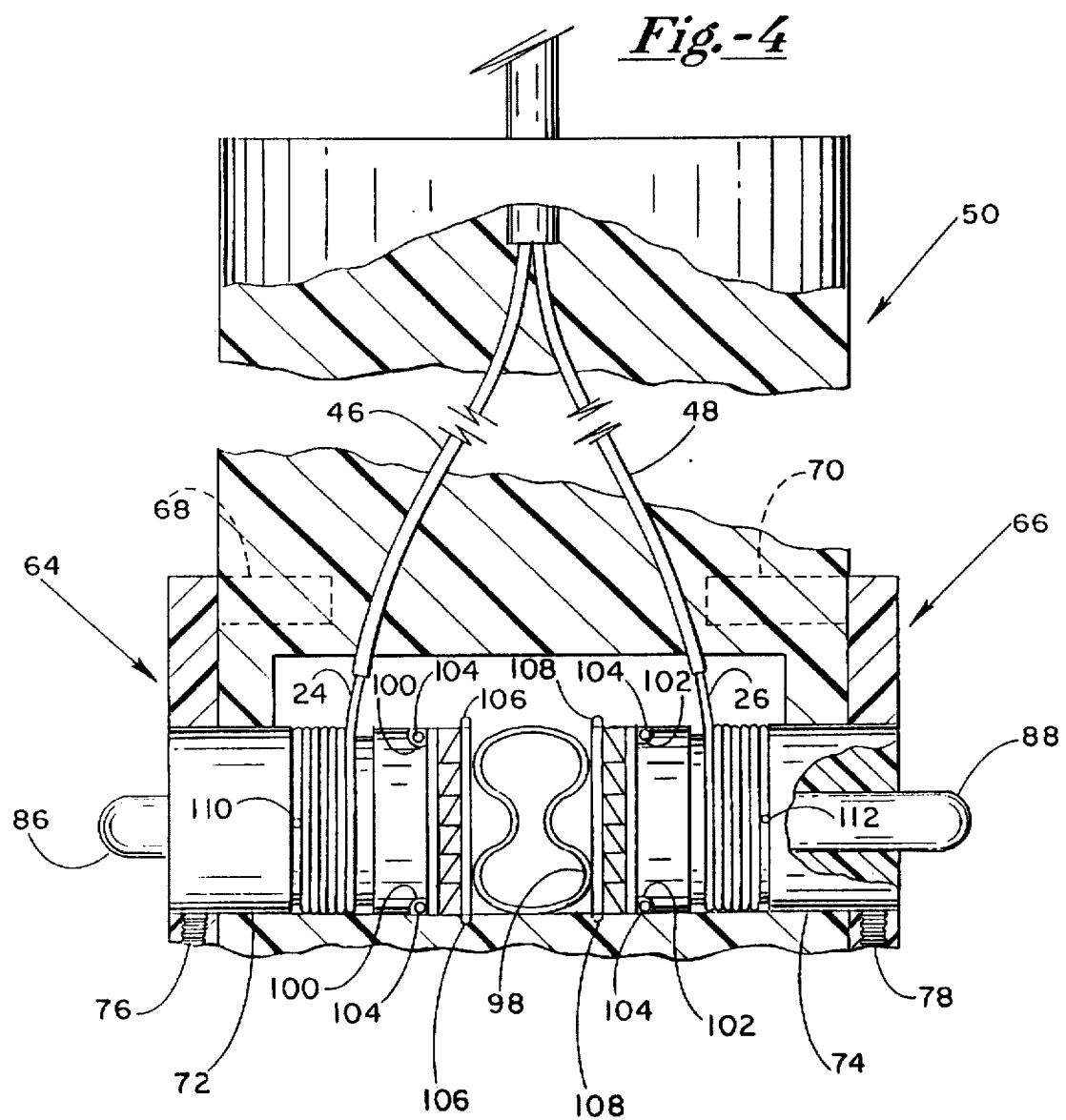
FIG. 4 is a schematic top view, broken, partially in section, with parts cut away of a catheter and handle for use with the electrode array.

One possible construction of the proximal end of and control handle elements for the catheter of the invention is illustrated in FIGS. 3-5. FIGS. 3A and 3B show the top and side view of the handle 50, generally. The catheter sheath 18 fits into the handle and the two bundles of electrical wires containing conductors connecting each electrode on the loop are threaded through the catheter tube segment 52 into and through the length of the handle to the proximal end of the handle 20 where they connect to a multi-pin input/output connector 54.

The two pull wires are attached to separate pull wire tension control systems and shown in greater detail in FIGS. 4 and 5. As seen in the exploded view of FIG. 5, the tension control systems and handle assembly include a pair of spaced symmetrical handle mechanisms. The tension control systems are shown in the form of opposite hand releasable ratchet mechanisms in which a pair of tension control lever members 64 and 66 with respective finger operated handle segments 68 and 70 are attached to hollow, generally cylindrical ratchet members 72 and 74 as by set screws 76 and 78. The ratchet members 72 and 74 have respective sets of unidirectionally engaging gear teeth 82 and 84 designed to cooperate with a resilient engaging and release mechanism which includes a pair of oppositely disposed locking members having shafts 86 and 88, designed to be journaled in bores 90 and 92 and having sets of gear teeth 94 and 96 disposed to mesh with respective teeth sets 82 and 84 as the locking members are urged outward by a spring member 98. As can best be seen in FIG. 5, the ratchet members 72 and 74 are provided with channels as at 100 and 102 which are designed to accommodate locking pins 104 when the tension control system is assembled in a handle bore 184 (FIG. 4).

As shown in FIG. 4, the loop deflection control wires 24 and 26 are threaded through openings 110 and 112 and attached to the ratchet members 72 and 74 and wound around them. Movement of the tension control lever handles 68 and 70 toward the proximal end of the handle draws the wires 24 and 26 and causes the loop to open. Each lever maintains its position upon release using the spring loaded gear tooth locking system which are caused to be continually engaged by the spring member 98. Rotation of the members 86 and 88 is prevented by two teeth 106 and 108, respectively, on each locking member that engage channels 103 (FIG. 4) in the handle member 50. Since each lever can be moved independently of the other, the deflection of the loop can be skewed or biased and thereby adjusted to better fit any shape of any chamber addressed. The tension on the deflection control wires is relieved individually by simply pushing in on the release knob ends of the members 86 and 88 to disengage the gear teeth and release the deflection control ratchet cylinder, allowing the corresponding handle to move back toward the closed loop position. To deflect or open the loop, the deflection control handle of interest can be moved without pressing the locking control knob, since the one-way locking teeth sets 82, 94 and 84, 96 slide on each other as a ratchet mechanism in one direction.

In operation, the catheter system is introduced by an incision into the vascular system of the patient and routed through the vascular system into the inferior vena cava such that the distal end of the main catheter extends into the right atrium chamber of the patient's heart. Once the proper position is reached, reciprocal movement of the handles 68 and 70 produces precise control of the size and shape of the loop 20 such that any point on the wall of the valve is readily accessible to the electrodes 36 of the ring 20. The distal tip of the catheter may also be extended through the tricuspid valve into the right ventricle-to address the ventricular side of the tricuspid valve with the loop 20. The electrode members 36 can be utilized to map the cardiac depolarization potentials throughout the valve folds and surfaces, thereby locating and mapping any early activation sites. The tip extension or guide provides leverage to stabilize the loop location for mapping and for tissue ablation.

The distal segment may also be provided in the form of an open, relatively fixed loop of any desired predetermined configuration (size or shape) to address any of many discrete cardiac chamber or valve areas. In this manner, any of the shapes assumable by the adjustable loop catheter system may be conveniently produced as a predetermined specialty shape for a particular application. Size variation to accommodate a plurality of heart sizes, of course, is also contemplated. Such fixed shape embodiments may include proximal or on-loop deflection control and may be provided with distal guide extensions as desired.

FIGS. 7A and 7B depict schematically but two of many possible catheter configurations, with elongated parts broken away, to illustrate the fixed shape concept. They include catheter handles as at 150 with tension control knobs 152 and proximal plug or jack connections 154 to connect a plurality of, possibly 24, electrical conductors. The main catheter tubes are shown broken away at 156. The short distal working catheter sections optionally include proximal segments connecting the loop with the main catheter which can be pre-shaped as desired are illustrated at 158 and 160. The segments 158 and 160 may be straight as shown in 160 or preformed in any desired curvature or other contortion suitable for proper placement in any particular application of the loop catheter. The loops are shown at 162 and 164 and these also may be any desired side and shape but are preformed so that when tension on the loop is released, the predetermined shape of both the segments 158 and 160 and the loops 162 and 164 is resumed. FIG. 7C illustrates a fragmentary view, with parts broken away, showing-how a typical loop might appear constrained within a catheter lumen or sheath. It will be appreciated that when the loops 162, 164 are stowed in the sheath or catheter, the opposite open sides are compressed together and so may be shaped such that facing sides are flat and parallel to enable them to nest better in the sheath or catheter lumen. This is illustrated in FIG. 7C in which a pair of loop segments 170 and 172 are shown as having facing sides which are flattened so that they readily come together for passage through the lumen 176 of the main catheter segment 156.

It is further noted that a tail segment, such as 166, may be used to guide and stabilize the manipulation of the loop within a valve and where specific areas are to be addressed, such a tail in the form of a loop or straight polymer segment may be used. It is also noted that at 168 and 169, control wires may be attached to the segments 158 and 160 to further control deflection of the loops in relation to the catheter as desired. Optionally, the wires may be attached anywhere on the loop itself as illustrated at 168A and 169A. These operate a tension-release mode in a well-known manner and may be attached similarly to those discussed as being attached to the deformable loops, above.

A plurality of electrodes 174 are arranged along the loops 162 and 164 and operated in the manner of those described in relation to the other embodiments. The electrodes 174 may preferably be conveniently arranged in pairs in which, for example, two electrodes approximately 2 mm in length are separated by a gap of approximately 0.5 to 1 mm. Typically, these pairs of electrodes are separated by a distance of approximately 8 mm. Of course, these dimensions are meant to be exemplary and, depending on the application, may be varied as desired.

The predetermined or fixed shape open loop electroded system is introduced much in the manner of the adjustable loop system. The main catheter is first navigated through the vascular system to the desired position relative to the chamber or valve of interest and the fixed loop distal catheter segment is deployed from a lumen therein, whereupon it resumes its predetermined shape. The control wires attachment as at 168 and 169 may be by pins 32, 34 in the manner illustrated in FIG. 1A, assist in fine control or maneuvering of the loop 158, 160 into any desired position. The guide segment 166 may also be employed in conjunction with the control wire to anchor the loop in a desired location.

Once the pre-shaped loop is positioned, the electrodes may be used to map the adjacent surface and the electrodes electrically ganged in any configuration to ablate tissue as indicated. Thus, ablation can be accomplished by energizing a single electrode, a pair of electrodes or more along the length of the loops as required. Of course, the loop position may be adjusted as required.

The fixed loop or loop of predetermined shape has been found to be quite advantageous in addressing certain locations to achieve accurate and rapid results. It must be kept in mind that the heart must continue to function all the while that the procedure is conducted and so the mapping or ablation tip device must follow tissue in almost constant motion.

An example of the use of the loop catheter is in the ablation of right-sided accessory pathways, modification for AV nodal reentry tachycardia and His bundle ablation which all require mapping and ablation along the perivalvular atrial tissues of the tricuspid ring. Since the tricuspid valve ring is directly accessible to catheters introduced from the major veins, so it provides an ideal setting for a loop-type structure, and particularly a fixed loop, which adapts to and addresses the valve ring with an array of recording/ablation electrodes. The most effective approach for tissue ablation around the tricuspid ring would be to map and immediately thereafter apply RF energy to the recording electrode which identifies the desired area to accomplish ablation.

One successful embodiment constructed and tested involved a deflectable fixed loop catheter equipped with 16, 4 mm long electrodes, spaced 4 mm apart. The most distal portion of the catheter was equipped with a small secondary guide loop. The catheter, introduced into the right atrium from the femoral vein, was found to be capable of adapting to the shape of the tricuspid ring when opened and was also capable of rotating across the valve plane by using a separate deflection control. The smaller secondary loop was anchored in the RV outflow and the proximal end was anchored by the inferior vena cava. Simultaneous recordings from the electrodes consisted of atrial and ventricular electrograms which could be adjusted by vertical and rotational movement of the catheter and by changing the deflection angle of the loop. The ablation electrodes on the loop catheter adapted well to the tricuspid ring orifice. Discrete perivalvular atrial sequential lesions were produced experimentally around the tricuspid valve without the need to readjust the catheter. Forty watts of RF energy was applied for 30 seconds to each of the ring electrodes, starting at the most distal electrodes, produced desired lesions. Placement of the catheter at the tricuspid ring position required minimal manipulation and catheter remained stable throughout the procedure.

The ease and precision of the mapping made possible with the catheter system of the invention makes location of early activation sites and ablation of associated tissue with respect to the tricuspid valve area much easier and more precise. This makes the procedure much more practical than previous systems.

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself. For example, the loop can be made to conform to a fixed predetermined shape such as a fully open loop upon being deployed as it emerges from the catheter lumen. Memoried materials such as flexible but memoried plastics, or metallic materials such as a nickel titanium alloy commonly known as nitinol, can be employed in such an embodiment.

I claim:

1. A cardiac catheter system comprising:
   (a) a main vascular catheter having a distal and a proximal end and capable of negotiating a vascular system to enter into a cardiac chamber of interest, the main catheter further describing an internal lumen extending from the proximal end to the distal end;
   (b) a recording and ablation working catheter system associated with the distal end of the main catheter and further including,
      (1) a lone open terminal loop of memoried shape self-assumed by said loop upon deployment subject to external constraining forces forming a portion of said working catheter system, the loop having an exterior surface and carrying an electrode array including a plurality of individual electrode means for performing procedures selected from the group consisting of recording and ablation, each said electrode means having an electrically conductive, externally exposed surface, the electrode array being arranged in spaced serial relation along the loop, the lone loop being freely maneuverable in said cardiac chamber of interest,
      (2) a relatively short intermediate segment joining the loop with the distal end of the main catheter and determining a relative posture between said loop and said main catheter,
      (3) insulated conductor means for connecting each of said electrode means individually with an electrical input/output device outside the catheter.

2. The apparatus of claim 1 wherein said relatively short intermediate segment has a predetermined resumable non-linear shape assumed upon deployment or removal of constraining forces.

3. The apparatus of claim 1 wherein the terminal loop further comprises an internal lumen and said insulated conductor means are threaded therethrough.

4. The apparatus of claim 1 further comprising deflection control wire means for modulating a posture of the loop with respect to that of the main catheter.

5. The apparatus of claim 4 wherein the deflection means is a pull wire anchored to said terminal loop.

6. The apparatus of claim 1 wherein said memoried shape self-assumed by said loop outside the catheter is one configured to address a specific area of said cardiac chamber of interest.

7. The apparatus of claim 1 further comprising distal guide means for assisting placement of the loop in a chamber of interest attached to said terminal loop.

8. The apparatus of claim 1 wherein said electrode means comprises spaced ring electrodes attached to said exterior surface of the said terminal loop.

9. The apparatus of claim 8 wherein said individual electrode means are approximately 2-5 mm in length.

10. The apparatus of claim 1 including control means connected to said conductor means in a manner such that said individual electrode means of said electrode array can be grouped together to be energized for operation in any desired manner for ablation, including for creation of lesions.

11. The apparatus of claim 10 wherein said individual electrode means are arranged in spaced pairs.

12. The apparatus of claim 11 wherein the pairs of electrode means consist of two electrodes approximately 2 mm in length, approximately 0.5 to 1.0 mm apart and wherein the pairs of electrodes are spaced approximately 8 mm apart.

13. The apparatus of claim 12 including control means connected to said conductor means such that said electrode means can be grouped together in any desired manner to be energized for ablation, including for creation of linear lesions.

14. The apparatus of claim 11 including control means connected to said conductor means such that said spaced pairs of said individual electrode means can be grouped together in any desired manner to be energized for ablation, including for creation of linear lesions.

15. The apparatus of claim 1 wherein said individual electrode means have at least one flattened surface.

16. A cardiac catheter system comprising:
  (a) a main vascular catheter having a distal and a proximal end, the main catheter further describing an internal lumen extending from the proximal end to the distal end;
  (b) a mapping ablation working catheter system, for recording and ablation in a predetermined cardiac chamber of interest, associated with and extending said main catheter and further including,
    (1) a lone open terminal loop of memoried shape self-assumed upon deployment forming a distal portion of said working catheter system, the loop having an exterior surface, a distal and a proximal extremity and carrying an electrode array including a plurality of individual electrode means for performing a function selected from the group consisting of recording and ablation, each having an electrically conductive externally exposed surface, the electrode array being arranged in spaced serial relation along said loop, the lone loop being freely maneuverable in said cardiac chamber of interest,
    (2) a relatively short intermediate segment joining said loop with said distal end of said main catheter,
    (3) insulated electrode conductor means for connecting each said electrode means individually with an electrical input/output device outside the catheter;
  (c) deflection control wire for modulating a posture of the loop with respect to that of the main catheter; and
  (d) control means connected to said electrode conductor means such that said electrode means can be grouped together in any manner for ablation.

\* \* \* \* \*